(12) United States Patent
Wolf et al.

(10) Patent No.: US 7,375,813 B2
(45) Date of Patent: May 20, 2008

(54) METHOD AND SYSTEM FOR DIFFUSION ATTENUATED TOTAL REFLECTION BASED CONCENTRATION SENSING

(75) Inventors: James D. Wolf, Kettering, OH (US); Robert E. Kauffman, Centerville, OH (US)

(73) Assignee: Eastman Kodak Company, Rochester, NY (US)

( * ) Notice: Subject to any disclaimer, the term of this patent is extended or adjusted under 35 U.S.C. 154(b) by 486 days.

(21) Appl. No.: 10/970,110

(22) Filed: Oct. 21, 2004

(65) Prior Publication Data

US 2006/0087654 A1 Apr. 27, 2006

(51) Int. Cl.
*G01N 21/00* (2006.01)

(52) U.S. Cl. .................. 356/433; 356/432; 356/445

(58) Field of Classification Search ................ 356/435, 356/436, 445
See application file for complete search history.

(56) References Cited

U.S. PATENT DOCUMENTS

| | | | |
|---|---|---|---|
| 3,449,051 A | 6/1969 | Levitt | |
| 3,669,545 A | 6/1972 | Gilby | |
| 3,902,807 A * | 9/1975 | Fleming et al. | 356/300 |
| 4,382,656 A | 5/1983 | Gilby | |
| 4,730,882 A | 3/1988 | Messerschmidt | |
| 5,035,504 A * | 7/1991 | Milosevic et al. | 356/300 |
| 5,164,589 A | 11/1992 | Sjoedin et al. | |
| 5,170,056 A | 12/1992 | Berard et al. | |
| 5,241,189 A * | 8/1993 | Vandagriff et al. | 356/435 |
| 5,373,366 A * | 12/1994 | Bowers | 356/435 |
| 5,452,083 A | 9/1995 | Wilks, Jr. | |
| 5,572,321 A | 11/1996 | Pinier et al. | |
| 5,835,231 A | 11/1998 | Pipino | |
| 6,067,151 A | 5/2000 | Salo | |
| 6,124,937 A | 9/2000 | Mittenzwey et al. | |

(Continued)

FOREIGN PATENT DOCUMENTS

EP 0 284 270 9/1988

(Continued)

OTHER PUBLICATIONS

Refractive Index Sensor With a Guided-Mode Resonant Grating Filter, p. 219—Optical Engineering for Sensing and Nanotechnology (ICOSN 2001), Koichi Iwata, Editor, Proceedings of SPIE vol. 4416 (2001), pp. 219-222.

(Continued)

*Primary Examiner*—Layla G. Lauchman
*Assistant Examiner*—Juan D Valentin, II

(57) ABSTRACT

A system for measuring light absorption levels for a liquid for use in a printing system includes a light source adapted to provide a divergent beam of light, a liquid container with a hole that acts as a focusing lens, and a prism disposed over the hole to split the divergent beam of light into a reference beam and a measurement beam. The systems include a measurement detector to measure the intensity of the focused beam to produce a liquid measurement signal. A reference detector measures the intensity of the reference beam for compensating the effects of temperature and light source variations on the system signals. A device calculates signal ratios and stores the ratios so that the signal ratios of subsequent colored liquids can be converted into colorant concentrations from a look-up table or through calculations using a signal ratio/colorant concentration.

29 Claims, 4 Drawing Sheets

U.S. PATENT DOCUMENTS

| | | | |
|---|---|---|---|
| 6,141,100 | A | 10/2000 | Burka et al. |
| 6,201,607 | B1 | 3/2001 | Roth et al. |
| 6,480,282 | B1 | 11/2002 | Chinowsky et al. |
| 6,504,651 | B1 | 1/2003 | Takatori |
| 7,221,440 | B2 * | 5/2007 | McCann et al. ............ 356/128 |
| 2002/0149775 | A1 | 10/2002 | Mori et al. |
| 2005/0007596 | A1 | 1/2005 | Wilks, Jr. et al. |
| 2006/0181709 | A1 * | 8/2006 | Wolf et al. ................ 356/436 |

FOREIGN PATENT DOCUMENTS

| | | |
|---|---|---|
| EP | 0 635 714 | 1/1995 |
| EP | 0 714 024 | 5/1996 |
| EP | 0671622 | 12/2000 |
| GB | 2 014 724 | 8/1979 |
| JP | 62 235546 | 10/1987 |
| JP | 2000 065730 | 3/2000 |
| WO | 88/01376 | 2/1988 |
| WO | 93/09421 | 5/1993 |
| WO | 02/077616 | 10/2002 |

OTHER PUBLICATIONS

New Technique for Determining the Optical Constants of Liquids, by C. Dale Keefe and Jason K. Pearson, Society for Applied Spectroscopy, vol. 56, No. 7, 2002-09728.

Absorption Measurement Using a Leaky Waveguide Mode, Optical Review vol. 4, No. 3 (1997) 354-357.

An Optical Fibre Refractometer for Liquids Using Two Measurement Channels to Reject Optical Attenuation, J. Phys. E: Sci. Instrum. 21 (1988) (64-67).

Absorption Sensor Based on Total Internal Reflection Diffraction Grating, Institute of Physics Publishing, J. Opt. A: Pure Appl. Opt. 4 (2002) 382-386.

Internal Reflection Spectroscopy by N. J. Harrick, New York, Interscience Publishers [1967].

* cited by examiner

METHOD AND SYSTEM FOR DIFFUSION ATTENUATED TOTAL REFLECTION BASED CONCENTRATION SENSING

CROSS REFERENCE TO RELATED APPLICATION

Reference is made to commonly assigned, copending application Ser. No. 11/395,785, filed Mar. 31, 2006, which is a continuation-in-part of this application.

FIELD OF THE INVENTION

The present embodiments relate to an optical method designed to monitor, on-line or on-site, the dye concentration of black and color inks used by printers or similar printing devices.

BACKGROUND OF THE INVENTION

Attenuated total reflectance techniques used to monitor the dye concentration of in-service printing inks use focusing lens, fiber optics, white light source, gratings to obtain required wavelengths, filters and other expensive, and vibration sensitive optical components. A need exists for a simple, rugged, and inexpensive optical method designed to monitor, on-line or on-site, the dye concentration of black and color inks used by printing presses that is much simpler in concept and much lower in cost than other optical systems currently on the market.

The present embodiments described herein were designed to meet these needs.

SUMMARY OF THE INVENTION

A system for measuring light absorption levels for a liquid for use in a printing system utilizing a light source to provide a divergent beam of light and a liquid-holding container with a hole that acts as a focusing lens. A prism is located over the hole to split the divergent beam of light into a reference beam and a measurement beam. A reference detector measures the intensity of the reference beam and produces a reference signal which is used to negate the effects of temperature on the detector output and variations in the light source output. A portion of the measurement beam passes through the hole to the liquid, is reflected back from the liquid, and is focused by the hole forming a focused beam.

A measurement detector measures the intensity of the focused beam and produces a liquid measurement signal which is related to the light absorption level of the liquid. The ratio of the liquid measurement signal to the reference signal is then calculated to determine the signal ratio which is related to the light absorption level of the liquid, and consequently, to the colorant concentration of the liquid.

The colorant concentration of the liquid is determined by comparing its signal ratio to the signal ratios of colorless and colored liquids with known colorant concentrations. The colorant concentration can be determined by using look-up tables containing a large number of stored signal ratios and corresponding colorant concentrations or by calculating the colorant concentration from the stored signal ratios of two liquids with known colorant concentrations.

BRIEF DESCRIPTION OF THE DRAWINGS

In the detailed description of the preferred embodiments presented below, reference is made to the accompanying drawings, in which.

The present embodiments are detailed below with reference to the listed Figures.

DETAILED DESCRIPTION OF THE INVENTION

Before explaining the present embodiments in detail, it is to be understood that the embodiments are not limited to the particular descriptions and that it can be practiced or carried out in various ways.

The present embodiments include an inexpensive and reliable system to monitor and calculate the light absorption values of fluids, such as liquid inks in a real time, one line continuous basis or as a batch method.

The system embodied herein contain very few parts, which make them less expensive than other systems, such as those with infrared fluorescent markers and readers, and they are easier to maintain, and highly reliable. Additionally, they are easy to incorporate into a manufacturing process for an ink jet printer, as they are small in size. The embodied systems can be easily modified into a portable unit.

The embodied systems and methods use a divergent beam of light. The divergent beam of light is less expensive to use than other forms of polarized or modified wavelengths.

The systems and methods of the invention are not sensitive to the thickness of the fluid flow through the unit, which makes them highly versatile and usable for many different kinds of inks.

These systems and methods provide a predictable and reliable result regardless of fluid flow rates and pressures. Even vibration has little effect on the calculated value with these systems and methods.

The present embodiments can also be used to calculate the ink concentration of two different inks simultaneously using only one container. The benefit of measuring two inks simultaneously makes the embodied systems highly versatile and adaptable for all colors of fluids and all types of inks and easy to use in a printer which has to use sequentially, different types of inks.

The embodied systems and methods can be used as an on-line sensor or can be miniaturized for use as a hand held device for on-site analysis. In contrast to other attenuated total reflectance systems that rely on fiber optics and lenses to focus light beams onto or from a reflective transparent surface, the embodied diffusion attenuated total reflectance system uses a hole formed into a container, wherein the hole is in contact with a glass or quartz prism surface to sample a diverging light beam and to focus the reflected light from that beam. Consequently, the diffusion attenuated total reflectance systems do not have the alignment issues or vibration sensitivity of attenuated total reflectance systems that use fiber optics, lenses to focus the light and gratings to produce specific wavelengths of light.

Figure 1:
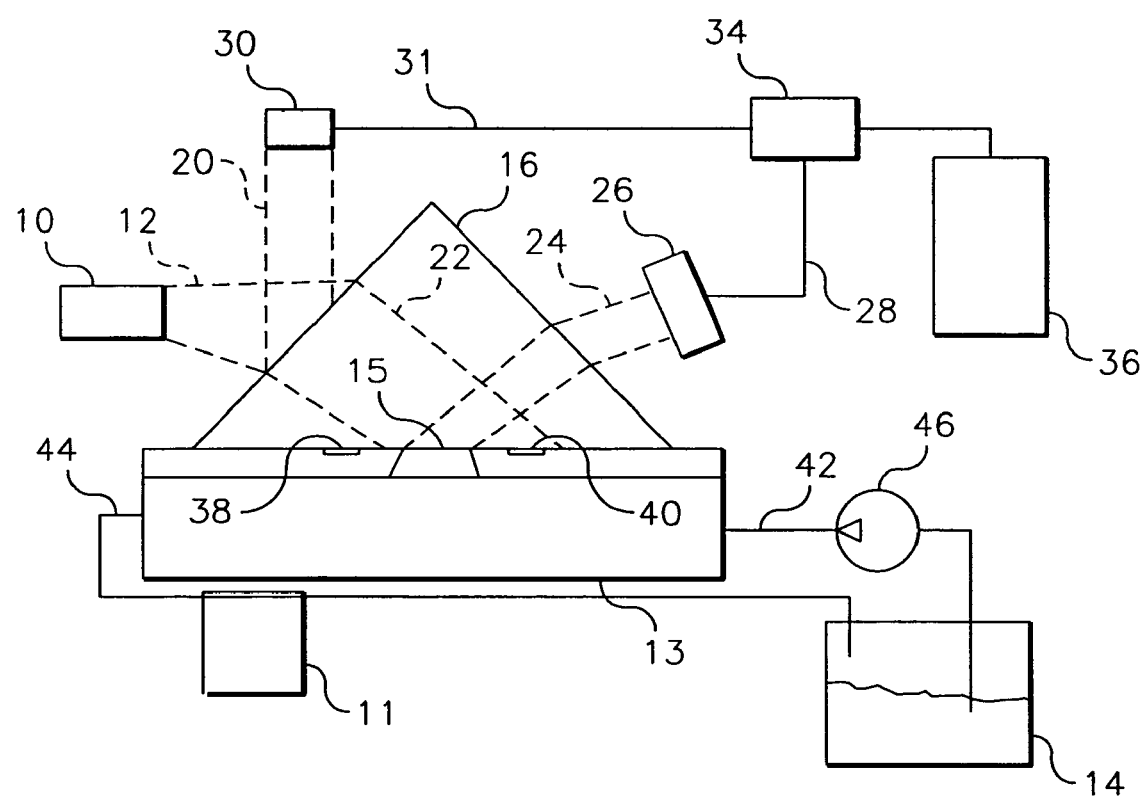
FIG. 1 depicts a cross section of an embodiment of the system.

With reference to the figures, FIG. 1 an embodiment of the system that measures light absorption levels for liquids in use in a printing system 11.

The liquids usable in the system include inks, toners, or colorless liquids. If the liquid is an ink, the ink can be an aqueous-based ink, a polymer-based ink, or a solvent-based ink. An example of a colorless liquid is a cleaning fluid, such as the Scitex Versapure 1045 Printhead Cleaning Fluid.

The system depicted in FIG. 1 involves a light source 10 adapted to provide a divergent beam of light 12. The light source is typically a visible light emitting diode (LED). The LED light source can be a red LED, a blue LED, a green LED, an amber LED, or a multi-color LED. The LED preferably emits a wavelength that is a highly absorbing wavelength for colored liquid. Other types of usable light sources include laser diodes, light bulbs, tungsten filaments, or similar light sources.

The system further utilizes a container 13 that is adapted to receive and hold a volume of liquid 14. In a preferred embodiment, the liquid 14 is colorless and is measured for light absorption levels. By measuring the colorless liquid, a base value is created that can be compared to light absorption levels of subsequent fluids that pass through the container.

In an alternative embodiment, the liquid 14 is a colored liquid ink or a toner which has a known colorant concentration. In this embodiment, the known colorant concentration is used as the base value for obtaining a value of what is later referred to as the reference signal. The base value is compared to light absorption levels of subsequent fluids that are passed through the container and measured and a series of computations is performed with this base value to ascertain ink concentration based on total attenuated reflectance of the fluid.

The container 13 in one embodiment has a hole 15 in one surface of the container enabling light from the divergent beam of light to impact the liquid. The hole 15 also acts as a focusing lens for light reflected by the fluid from the divergent beam of light.

Figure 2:
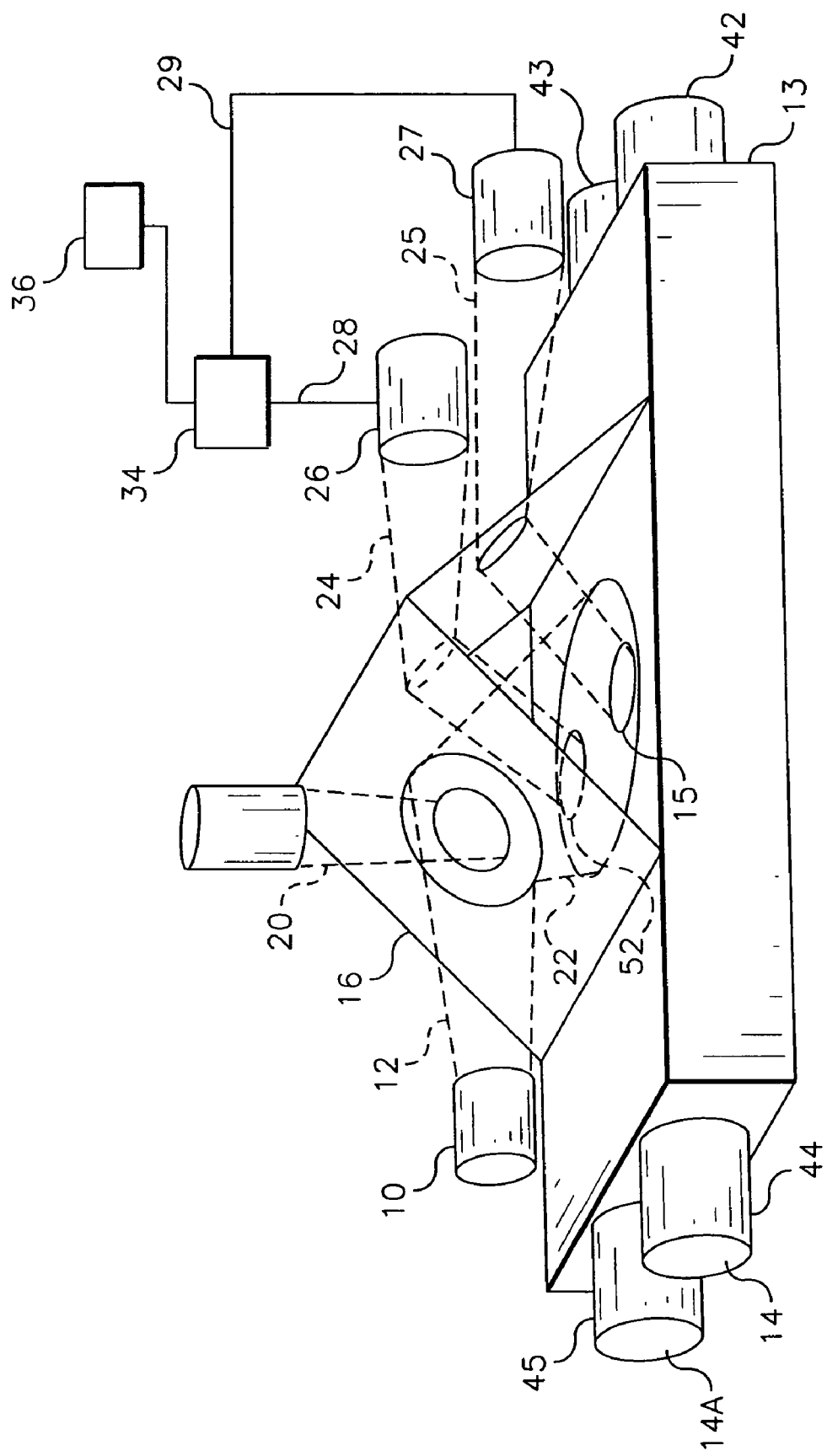
FIG. 2 depicts a side perspective view of a different embodiment of the system.

The container 13 can be constructed in different variations. FIG. 2 depicts an embodiment of container 13, wherein the container 13 has two channels for flowing liquid and two holes. In still other embodiments, it is contemplated that the container 13 is simply a box, with only opening to receive one or more samples of fluid, and a hole or plurality of holes for hand held batch measurement, without the on line design of FIG. 1.

The container 13 is preferably made of a material that is not easily subject to degradation by ultra-violet (UV) light or by chemicals. Preferred materials for the container include stainless steel or Delrin™, a material available from Dupont of Wilmington, Del. The container 13 needs to be made from a material which can be easily machined so that channels and holes can be formed in the container 13 without raw edges. Acetyl resin is another material acceptable for the construction of the container 13.

Continuing with FIG. 1, the container 13 has an inlet 42 and an outlet 44 for permitting the liquid to enter the container 13 and exit the container 13, respectively. Typically, the flow rate of liquid through the container is contemplated to be between 0.1 liters per minute and 1 liters per minute, but the system can be modified to handle larger flow rates. One or more pumps 46 can be connected to the container 13 to facilitate movement of liquid through the container. A liquid source can engage the pump in order to flow liquid in an uninterrupted and continuous manner through the container 13. The pump 46 can be a liquid pump, such as a gear driven pump from Micropump Corporation.

In an alternative embodiment, the container 13 includes only an inlet 42 and the hole 15. The container 13 can be used for a batch process, wherein the container 13 holds a static, non-flowing volume of liquid that is used to measure the reflective index of the liquid in the container, such as up to 8 liters of fluid. The container could have more than one compartment for measuring two fluids or more in this static or batch method.

In still another embodiment, a non-reflective coating 40 can be added to the container to control and ensure that a non-focused light beam does not come in contact with the measurement detector. Examples of usable coatings include Black Delrin™ and other black, non-flaking non-glossy paints that are stable and do not degrade in the presence of light. Preferably, the coating is only disposed on the surface of the container 13 that is in contact with a prism 16 disposed over the hole 15 which is discussed below.

The prism 16 is disposed over hole 15 to split the divergent beam of light into a reference beam 20 and a measurement beam 22. The one prism can be place over more than one hole and still used in this method. The prism 16 is typically glass or quartz, but the prism 16 material is not limited to these materials. Usable prisms 16 can be readily obtained from Edmonds Scientific and other high quality glass sources, including Corning Glass of Binghamton, N.Y. Although triangular shaped ninety-degree glass prisms are depicted in the figures, other styles and shapes of prisms can be used. Additionally the prisms can made of different optically clear materials such as sapphire and still used in these embodiments.

The prism 16 is preferably sealed over the hole 15 in a leak tight manner using a seal 38 or sealing material, such as an adhesive sealing material. The seal 38 can be an O-ring, such as elastomeric O-ring; or a gasket, such as EPDM or a terpolymer elastomers made from ethylene propylene diene-monomer or butyl amide gaskets. Alternatively, a clamp can be used to hold the prism 16 over the one or more holes.

A reference detector 30 and a measurement detector 26 are preferably placed beneath the prism 16 and the hole 15. By placing the detectors 26 and 30 beneath the prism 16 and hole 15, the chance of bubbles in the liquid interfering with the measurement detector 26 is reduced when the prism is inverted. The reference detector 30 measures the intensity of the reference beam 20. Known reference detectors are readily available and can be procured though Radio Shack for very little money.

A portion of the divergent beam is reflected from the surface of the prism 16 and to the reference detector 30 forming a reference signal 31. The liquid reference signal 31 is used to compensate for the effects of temperature and light source variations with regard to the intensity of the light source. As a further precaution, a housing (not shown) optionally can be used to enclose completely the entire system, including container, prism, and detectors to protect the device from the elements or dirt in a printing house, or other problems, such as dripping water which could dilute or otherwise effect the sample or the quality of reflected light to be measured.

Figure 4:
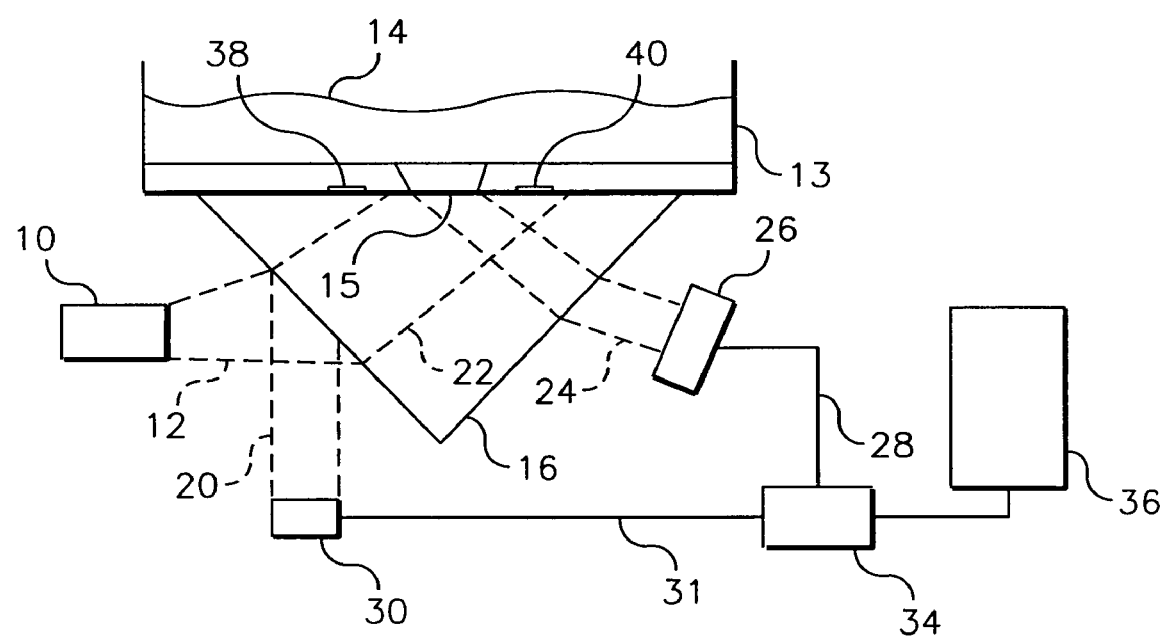
FIG. 4 depicts a cross section of the second embodiment of the system when used as a batch measurement system.

A portion of the measurement beam 22 passes through the hole 15 to the liquid and is reflected back from the liquid through the hole, which acts as a focusing lens, into the prism 15 as shown in FIGS. 1, 2 and 4. The beam reflected back from the liquid is focused by way of the hole 15, forming a focused beam 24 which is reflected in the prism 15 as shown in FIGS. 1, 2 and 4.

The measurement detector 26 can be any known measurement detector for light, such lights sensors available from Radio Shack. The measurement detector is used to measure the intensity of the focused beam to determine a light absorption level of the liquid, which is either the colorless liquid or the colored liquid with the known colorant value. The intensity of the focused beam is related to the light absorption level of the liquid. The measurement detector 26 then produces a first liquid measurement signal 28. The measurement detector 26 can be a light sensor that produces a voltage and the voltage can then be measured using a simple voltage measurement device such as a volt meter. The measurement device not only measures the first or colorless liquid value, but then the ink of interest is places in the container and a similar measurement is performed forming a colored liquid measurement signal. Additionally, a colored liquid reference signal is formed in the same manner as the colorless liquid reference signal already described.

Device 34 makes simple mathematical calculations to determine the signal ratio of the liquid based on the four detected values described above. Device 34 can be a logic circuit or a microprocessor, or a PC. The device 34 uses the following formula as the basis for the calculations:

$$SR = LMS/RF$$

Wherein
SR=Signal Ratio
LMS=Liquid Measurement Signal
RS=Reference Signal

Typically the device 34 can be other than a PC or microprocessor, and PDAs, laptops, even cell phones or calculators can be used as Device 34.

The embodied systems further include software, such as a look-up table or colorant concentration calculation 36, installed on the device 34. The look-up table or colorant concentration calculation 36 is typically constructed by the user of the device by running colorless and colored liquids of known concentrations through the device 34 and recording the signal ratio values into the look-up table or determining the slope of the linear plot produced by plotting the light absorption values of a colorless liquid and of liquid(s) with known colorant concentration(s) versus the colorant concentration of the colored liquids 36. The following formula is used to calculate the light absorption values of the colorless and colored liquids $$LAV = 1 - SR/SR'$$

Wherein:
LAV=Light Absorption value
SR=Signal ratio of Colored Liquid
SR'=Signal Ratio of Colorless Liquid The embodied systems and methods are utilized to monitor the dye concentration of in-service printing inks using diffusion attenuated total reflectance of the fluids.

The following is an example of one way to use the system. A light from a source, such as a red LED, produces a divergent beam of light against the angled surface of the prism which is disposed over the hole in the container as described above. A portion of the light is reflected by the angled surface and measured by a reference detector. The light measured by the reference detector is used to monitor the output of the light source and the effects of temperature on the detector efficiency. Of the produced light passing through the prism, only the light that comes into contact with the prism surface above the hole in the container is sampled and focused onto the signal detector. A portion of the light, sampled by the hole, is absorbed by the ink filling the hole. The absorbance of the light is inversely proportional to the concentration of the dye in the ink. For example, the detector signal decreases (absorbance increases) as the dye concentration increases. The light detected by the signal detector is compared to the light detected by the reference detector to negate the effects of variations in the light output or detector temperature on the determined dye concentration.

An interchangeable LED can be used in this system. Realignment is not needed when the LED is changed due to malfunction or to a change in the ink color being used in the printer system. For example, a red LED works best for cyan colored inks while a green LED works best for magenta colored inks.

FIG. 2 depicts an alternative embodiment, wherein two liquids are used for measuring light absorption levels for a liquid for use in an ink jet printing system. The system for two liquids includes a second inlet 43 to allow the second liquid 14a to enter the container 13. The system has a second outlet 45 to allow the second liquid 14a to exit the container 13. The container 13 includes a second hole 52 that allows the divergent beam to be directed toward the second liquid 14a. Since two liquids and used, a second focused beam 25 and a second liquid measurement signal 29 are produced. A second measurement detector 27 is used to measure the intensity of the second focused beam and produce a second liquid measurement signal 29.

Optional filters can be placed in front of the measurement detectors to remove unwanted wavelengths of light coming into contact with the detectors.

Figure 3:
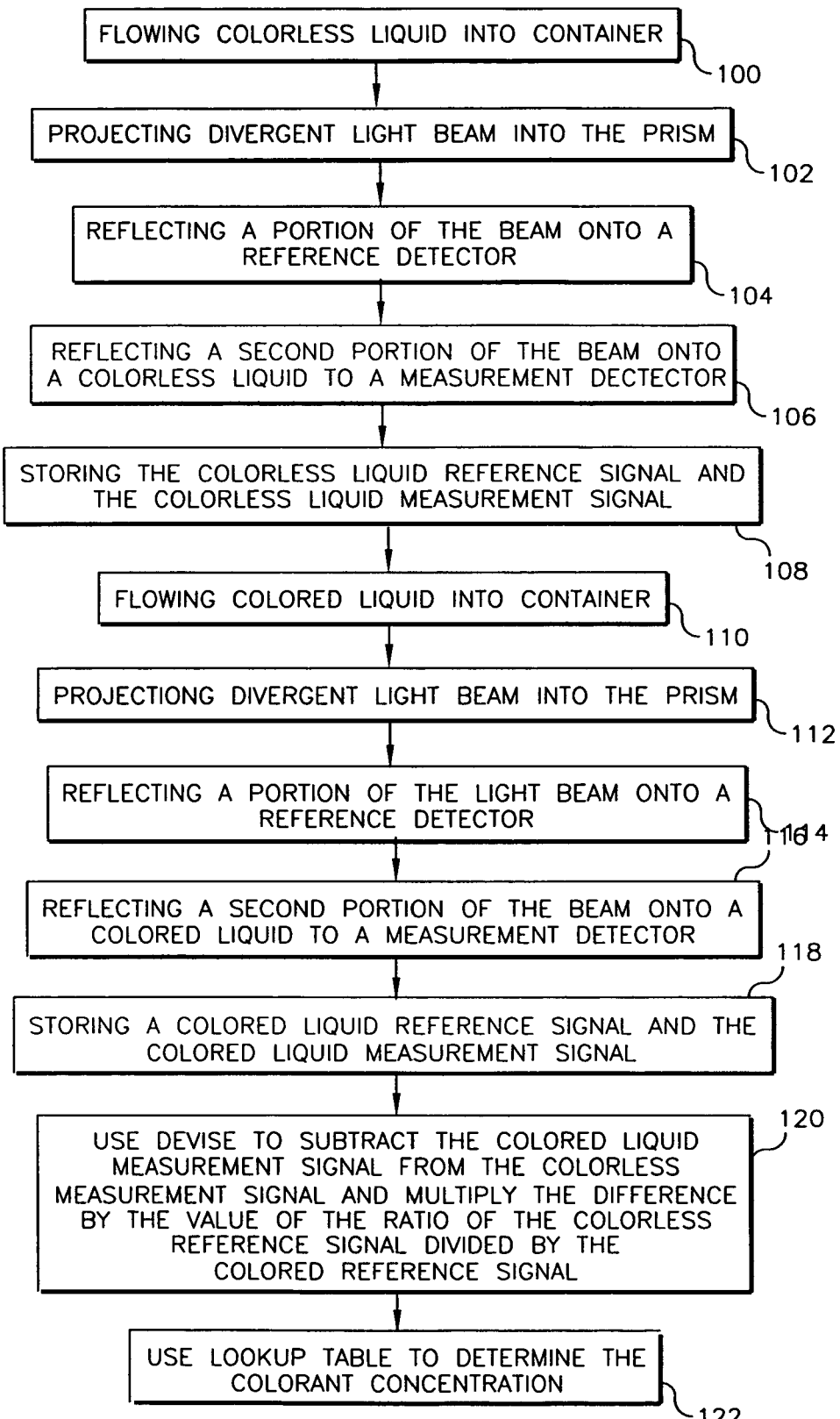
FIG. 3 depicts a block diagram of the method of the embodiment of FIG. 1.

FIG. 3 is a diagram of a preferred embodiment of the method for measuring light absorption levels of a liquid to control colorant concentration of the liquid for use in an ink jet printing system.

The methods involve measuring light absorption levels of a first liquid, such as a colorless liquid, and a second liquid, such as a colored liquid, to control colorant concentration of the colored liquid for use in a printing system. In an alternative embodiment, light absorption levels can be measured simultaneously for a colorless liquid and a colored liquid. In another embodiment, two colored liquids can be measured simultaneously. The printing system is typically an ink jet printing system.

The embodied methods entail flowing colorless liquid into a container 13 with a hole and a prism disposed over the hole (Step 100). Preferably, the prism is oriented so that air bubbles do not interfere with the measurement beam. In the alternative embodiment mentioned above, a first liquid flows into a first channel of the container having a first hole and a second liquid flows into a second channel of the container having a second hole. The first and second fluids flow into the respective channels simultaneously for this embodiment. For the two channel embodiment, both holes have the same prism disposed over the holes.

The methods continue by projecting a divergent beam of light from a light source onto the prism (Step 102) and reflecting a first portion of the divergent beam from the prism to a reference detector to measure intensity of the divergent beam and obtain a reference signal (Step 104).

A second portion of the divergent beam is passed through the prism onto the hole onto the colorless liquid. Light reflects from the fluid forming a light beam that is focused by the hole forming a focused beam of reflected light. The focused beam is measured by a measurement detector (Step 106). The measurement detector provides a colorless liquid measurement signal.

Alternatively, two portions of the divergent beam can pass through the prism and through both the first and second holes. The light passing through the first hole reflects onto the first liquid and the light passing through the second hole reflects onto the second liquid, which is typically a liquid of known colorant concentration. The light reflects back through both holes, and is focused by the holes, forming two focused beams. Each beam passes to a measurement detector to obtain a first and a second liquid measurement signals. The reference and liquid measurement signals can be stored for later use (Step 108).

Colored liquid then flows into the container (Step 110). Divergent light beam is projected into the prism (Step 112). The first portion of the divergent beam is reflected from the prism to a reference detector to measure intensity of the divergent beam and obtain a reference signal (Step 114).

A second portion of the divergent beam is passed through the prism onto a hole onto the colored liquid. A focused light beam is reflected from the colored liquid to a measurement detector (Step 116). The hole acts as a focusing lens to focus the light. The measurement detector provides a colored liquid measurement signal.

The method ends by computing simple mathematical equations from the measured signals (Step 120) to determine the colorant concentration of the liquid by comparing its light adsorption value to those of liquids of known colorant concentration. The mathematical equations are computed using a device 34, such a microprocessor, a computer, or circuitry that enables simple mathematical calculations to occur.

A look-up table (Step 122) can be used. The look-up table is used to find light absorption values of the measured liquid to determine the concentration of the colorant in the measured liquid. Signal ratio/colorant concentration factors can be used to calculate the concentration of the colorant in the liquid. The signal ratio/colorant concentration factor can be derived from measurements with the system using a colorless liquid, a liquid with a known colorant concentration, or a toner with a known colorant concentration.

The embodied methods can be used for a steady state flow of liquid through the container or can be used for a batch process.

FIG. 4 depicts the embodiment of the system used for the batch process. The batch system is similar to the steady-state system, but the container 13 holds a static, non-flowing volume of liquid 14.

The embodiments have been described in detail with particular reference to certain preferred embodiments thereof, but it will be understood that variations and modifications can be effected within the scope of the embodiments, especially to those skilled in the art.

PARTS LIST

10 light source
11 printing system
12 divergent beam of light
13 container
14 first liquid
14 second liquid
15 hole
16 prism
20 reference beam
22 measurement beam
24 focused beam
25 second focused beam
26 measurement detector
27 second measurement detector
28 liquid measurement signal
29 second liquid measurement signal
30 reference detector
31 reference signal
34 device
36 look-up table
38 seal
40 non reflective coating
42 inlet
43 second inlet
44 outlet
45 second outlet
46 pump
52 second hole
100 Step—flowing colorless liquid into container
102 Step—projecting divergent light beam into prism
104 Step—reflecting a portion of the beam onto a reference detector
106 Step—reflecting a second portion of the beam onto a colorless liquid to a measurement detector
108 Step—storing the colorless liquid reference signal and the colorless liquid measurement signal
110 Step—flowing colored liquid into container
112 Step—projecting divergent light beam into the prism
114 Step—projecting divergent light beam onto a reference detector
116 Step—reflecting a second portion of the beam onto a colorless liquid to a measurement detector
118 Step—storing a colored liquid reference signal and the colored liquid reference measurement signal
120 Step—using a device to calculate the value
122 Step—using a lookup table to determine the colorant concentration

The invention claimed is:

1. A system for measuring light absorption levels for a liquid for use in a ink jet printing system, wherein the system comprises:
   a. a light source adapted to provide a divergent beam of light;
   b. a container adapted to receive a liquid, wherein the liquid has a light absorption level;
   c. a hole in the container to provide access to the liquid, wherein the hole is capable of focusing light reflected back from the liquid in the container and through the hole;
   d. a prism disposed over the hole to split the divergent beam of light into a reference beam and a measurement beam before the light can pass through the hole to the liquid, wherein the reference beam has a reference beam intensity and does not pass through the hole to the liquid, wherein a portion of the measurement beam does pass through the hole to the liquid, is reflected back from the liquid and through the hole into the prism, and is focused by the hole to form a focused beam of light that is reflected via the prism and has a focused beam intensity;
   e. a measurement detector adapted to measure the focused beam intensity, wherein the measurement detector produces a liquid measurement signal, wherein the liquid measurement signal is inversely related to the light absorption level of the liquid;
   f. a reference detector adapted to measure the reference beam intensity forming a reference signal; and
   g. a device adapted to receive the liquid measurement signal and the reference signal, wherein the device computes a ratio of the liquid measurement signal to the reference signal to determine a signal ratio, wherein the signal ratio is inversely related to the light absorption level of the liquid.

2. The system of claim 1, further comprising a look-up table for comparing the signal ratio to the look-up table to obtain a concentration of colorant in the liquid.

3. The system of claim 2, wherein the look-up table is derived from measurements with the system using a colorless liquid, a liquid with a known colorant concentration, or a toner with a known colorant concentration.

4. The system of claim 1, further comprising a light absorption value/colorant concentration factor to calculate the concentration of the colorant in the liquid.

5. The system of claim 4, wherein the light absorption value/colorant concentration factor is derived from measurements with the system using a colorless liquid, a liquid with a known colorant concentration, or a toner with a known colorant concentration.

6. The system of claim 1, further comprising a seal between the prism and the container.

7. The system of claim 6, wherein the seal is a member of the group consisting of an adhesive, an o-ring, and a gasket.

8. The system of claim 7, wherein the o-ring is an elastomeric o-ring.

9. The system of claim 1, wherein the light source is a visible light emitting diode (LED).

10. The device of claim 9, wherein the LED is a member of the group consisting of red LED, a blue LED, a green LED, an amber LED, and a multiple color LED.

11. The system of claim 1, wherein the light source is a member of the group consisting of a laser diode, a light bulb, and a tungsten filament.

12. The system of claim 1, wherein the container is adapted to flow liquid at a flow rate ranging between 0.1 liters per minute and 10 liters per minute.

13. The system of claim 12, wherein the container is adapted to flow liquid at a flow rate between 0.1 liters per minute and 1 liters per minute.

14. The system of claim 1, wherein the container adapted for batch measurement of a static liquid.

15. The system of claim 1, wherein the container further comprises:
   h. a first channel adapted to receive a first liquid;
   i second channel adapted to receive a second liquid;
   j. a first hole adapted to reflect and focus the light for the first liquid; and
   k. a second hole adapted to reflect and focus the light for the second liquid.

16. The system of claim 1, further comprising a coating on the container located where the container contacts the prism.

17. The system of claim 1, wherein the prism is a quartz prism or a glass prism.

18. The system of claim 1, wherein the prism is disposed on a side of the container to insure air bubbles rise away from the measurement beam.

19. The system of claim 1, wherein the measurement detector is a light sensor.

20. The system of claim 1, further comprising a pump adapted to flow liquid through the container.

21. A method for measuring light absorption levels of a liquid to control colorant concentration of the liquid for use in an ink jet printing system, wherein the method comprises the steps of:
   l. disposing a first liquid into a container having a hole, and a prism disposed over the hole, wherein the hole is capable of focusing light reflected back from the liquid in the container and through the hole into the prism;
   m. projecting a divergent beam of light from a light source onto the prism;
   n. reflecting a first portion of the divergent beam from the prism to a reference detector to measure divergent beam intensity and obtaining a first reference signal;
   o. passing a second portion of the divergent beam through the prism and through the hole onto the first liquid, reflecting the second portion back from the first liquid and through the hole into the prism so as to focus the second portion to be reflected via the prism towards a measurement detector, and obtaining a first liquid measurement signal;
   p. computing a first signal ratio based on the first liquid measurement signal and the first reference signal, wherein the first signal ratio inversely relates to the light absorption level of the first liquid;
   q. flowing sequentially a second liquid into the container;
   r. projecting the divergent beam of light from the light source onto the prism;
   s. reflecting the first portion of the divergent beam from the prism to the reference detector to measure divergent beam intensity and obtain a second liquid reference signal;
   t. passing the second portion of the divergent beam through the prism and through the hole onto the second liquid, reflecting the second portion back from the second liquid and through the hole into the prism so as to focus the second portion to be reflected via the prism towards a second measurement detector to obtain a second liquid measurement signal;
   u. computing a second signal ratio based on the second liquid measurement signal and the second reference signal, wherein the second signal ratio inversely relates to the light absorption level of the second liquid; and
   v. compare the signal ratio of the first liquid to the signal ratio of the second liquid to determine the light absorption value of the second liquid relative to the first liquid.

22. The method of claim 21, further comprising the step of comparing the light absorption level of the second liquid to a look-up table to determine the concentration of the colorant in the second liquid.

23. The method of claim 21, further comprising the step of comparing the light absorption level of the second liquid to a signal ratio/colorant concentration factor to determine the concentration of the colorant in the second liquid.

24. The method of claim 21, wherein the first liquid is a replenisher or colorless liquid and the second liquid is ink or toner.

25. The method of claim 21, wherein the method is a batch method for measurement.

26. A method for measuring light absorption levels simultaneously of a first liquid and a second liquid to control colorant concentration of the second liquid for use in an ink jet printing system comprising the steps of:
   w. flowing the first liquid into a first channel of a container wherein the first channel has a first hole and a prism disposed over the first hole, and wherein the first hole is capable of focusing light reflected back from the liquid in the container and through the hole into the prism;
   x. projecting a divergent beam of light from a light source onto the prism;
   y. reflecting a first portion of the divergent beam from the prism to a reference detector to measure intensity of the divergent beam and obtain a reference signal;
   z. passing a second portion of the divergent beam through the prism and through the first hole onto the first liquid and reflecting the second portion back from the first liquid and through the first hole into the prism so as to focus the second portion to be reflected via the prism towards liquid to reflected via the prism towards a first measurement detector to obtain a first liquid measurement signal;

aa. simultaneously with the flowing of the first liquid into the first container, flowing a second liquid into a second channel in the container, wherein the second channel has a second hole and the prism is also disposed over the second hole, and wherein the second hole is capable of focusing light reflected back from the liquid in the container and through the hole into the prism;

bb. passing a third portion of the divergent beam through the prism and through the second hole onto the second liquid and reflecting the third portion back from the second liquid and through the second hole into the prism so as to focus the third portion be reflected via the prism towards a second measurement detector to obtain a second liquid measurement signal;

cc. computing a first signal ratio, which is inversely related to the light absorption level of the first liquid, using the reference signal and the first light measurement signal;

dd. computing a second signal ratio, which is inversely related to the light absorption level of the second liquid, using the reference signal and the second light measurement signal; and ee. comparing the first signal ratio and the second signal ratio to determine the colorant concentration of the first liquid based on the colorant concentration of the first liquid.

27. The method of claim 26, further comprising the step of comparing the light absorption value of the second liquid to a look-up table to determine the concentration of the colorant in the second liquid.

28. The method of claim 26, wherein the second liquid is ink or toner.

29. The method of claim 26, wherein the method is a batch method for measurement.

* * * * *